United States Patent
Sutoris et al.

(10) Patent No.: US 6,726,854 B2
(45) Date of Patent: Apr. 27, 2004

(54) INHIBITOR COMPOSITION FOR STABILIZING SUBSTANCES CAPABLE OF FREE RADICAL POLYMERIZATION

(75) Inventors: Heinz Friedrich Sutoris, Frankenthal (DE); Gerhard Wagenblast, Wachenheim (DE); Volker Schliephake, Schifferstadt (DE); Jürgen Schröder, Ludwigshafer (DE); Harald Keller, Ludwigshafer (DE); Thomas Jaworek, Kallstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/201,936

(22) Filed: Jul. 25, 2002

(65) Prior Publication Data

US 2003/0097017 A1 May 22, 2003

Related U.S. Application Data

(62) Division of application No. 09/634,890, filed on Aug. 7, 2000.

(30) Foreign Application Priority Data

Aug. 17, 1999 (DE) .......................... 199 38 841

(51) Int. Cl.⁷ .................... C09K 15/30; C09K 15/32; C09K 15/08; C07D 211/60
(52) U.S. Cl. ................. 252/400.21; 546/210; 546/184; 546/265; 548/841; 548/542
(58) Field of Search ................ 546/210, 184, 546/245; 252/400.21; 548/841, 542

(56) References Cited

U.S. PATENT DOCUMENTS

| | | | |
|---|---|---|---|
| 3,818,079 A | 6/1974 | Sato et al. | |
| 4,187,382 A | 2/1980 | Cowherd, III et al. | |
| 5,322,960 A | 6/1994 | Sakamoto et al. | |
| 6,200,460 B1 | 3/2001 | Sutoris et al. | |
| 6,458,956 B1 * | 10/2002 | Sutoris et al. | 546/210 |

FOREIGN PATENT DOCUMENTS

| | | |
|---|---|---|
| DE | 29 13 218 | 10/1980 |
| DE | 19651 307 A1 | 6/1998 |
| DE | 19707 151 A1 | 8/1998 |
| EP | 0 620 206 A1 | 4/1994 |
| WO | WO 00/36052 | 6/2000 |

OTHER PUBLICATIONS

Wolf D. Hablcher, et al., Interactions of Stabilizers During Oxidation Processes, (1997), pp. 93–125.

* cited by examiner

Primary Examiner—Rita Desai
(74) Attorney, Agent, or Firm—Oblon, Spivak, McClelland, Maier & Neustadt, P.C.

(57) ABSTRACT

An inhibitor mixture containing, as components, a) at least one nitroxyl radical (derivative), b) at least one phenol (derivative) and c) at least one chemical compound which contains at least one phosphorus atom which has the oxidation state +3 is preferably used for stabilizing compounds capable of free radical polymerization.

6 Claims, No Drawings

INHIBITOR COMPOSITION FOR STABILIZING SUBSTANCES CAPABLE OF FREE RADICAL POLYMERIZATION

This application is a division of application Ser. No. 09/634,890 filed on Aug. 7, 2000.

The present invention relates to an inhibitor composition and its use for stabilizing substances capable of free radical polymerization, and a mixture containing the inhibitor composition.

Many compounds which have one or more vinylically unsaturated groups have a pronounced tendency to free radical polymerization. Such compounds are also used specifically as monomers for free radical polymerization. At the same time, however, the pronounced tendency to free radical polymerization is a disadvantage in that undesired free radical polymerization of the vinylically unsaturated compounds can occur both during storage and during chemical and/or physical processing (for example distillation or rectification), in particular under the action of heat and/or light. Undesired free radical polymerization can have various adverse effects, especially if polymer is precipitated. For example, in the distillation of vinylically unsaturated compounds, polymer formed by free radical polymerization may be deposited on the surface of the evaporator used—the tendency to free radical polymerization is particularly pronounced there owing to the high temperature. Polymerization in the region of the surface of an evaporator generally means that a polymer layer forms on the surface. Owing to the insulating effect of the polymer layer, the heat transfer is reduced in an undesired manner. Undesired polymer formed by free radical polymerization can, however, also block the internals of rectification columns, which causes undesired pressure drops. The deposition of polymer may finally necessitate stoppage of the rectification process, since the deposited polymer has to be removed in order to continue the rectification.

It is therefore general practice to add compounds which act as inhibitors or retarders of free radical polymerization to vinylically unsaturated compounds capable of free radical polymerization and mixtures which contain such compounds. While inhibitors suppress the free radical polymerization, including their complete reaction with free radicals, retarders slow down the free radical polymerization. Inhibitors and retarders are generally combined under the general term stabilizers. Below, however, both inhibitors and retarders are to be understood as meaning inhibitors. The use of inhibitors or retarders is of importance both during storage and during chemical and/or physical treatment (for example in distillation) of vinylically unsaturated compounds capable of free radical polymerization.

U.S. Pat. No. 4,187,382 relates to a process for the esterification of organic diols with acrylic acid. It is recommended to pretreat the diol with triphenyl phosphite in order thus to reduce the tendency of the reaction mixture to free radical polymerization. A phenolic polymerization inhibitor is proposed as a further inhibiting component.

DE-A 29 13 218 discloses a process for the preparation of acrylates or methacrylates, in which the polymerization inhibitor used comprises organic phosphites together with phenolic polymerization inhibitors.

The abovementioned inhibitor compositions contain phosphorus compounds which have phosphorus in the oxidation state +3 and further phenolic compounds. One object is further to improve the action of such systems in the stabilization of vinylically unsaturated compounds.

It is an object of the present invention to provide a highly active inhibitor composition which contains chemical compounds having phosphorus in the oxidation state +3 and/or phenolic compounds. This inhibitor composition should be particularly effective in that the inhibiting effects of the components present in it should reinforce one another in a synergistic manner.

We have found that this object is achieved by providing an inhibitor composition containing, as components, a) at least one nitroxyl radical (derivative), b) at least one phenol (derivative) and c) at least one further chemical compound which contains at least one phosphorus atom which has the oxidation state +3.

The oxidation state of an atom within a covalent compound is to be understood as meaning a number which has a positive or negative sign and indicates the charge which the atom would have if the bonding electron pairs of the covalent bonds in which the atom participates were assigned to the more electronegative bonding partner in each case. In the case of electron pairs of covalent bonds between two identical atoms, each atom contains one electron. The electronegativity is to be regarded here as a measure of how strongly an atom in a molecule attracts bonding electron pairs which are bonded to the atom. The electronegativities relevant at present are those according to H. R. Christen, Grundlagen der allgemeinen und anorganishcen Chemie, Verlag Sauerländer, Aarau, Diesterweg-Salle, Frankfurt am Main (1973). For the most important elements of the Periodic Table, these electronegativities have the following values:

Be (1.5); B (2.0); H (2.1); C (2.5); Si (1.8); Ge (1.7); N (3.0); P (2.1); As (2.0); Sb (1.8); O (3.5); S (2.5); Se (2.4); Te (2.1); F (4.0); Cl (3.0); Br (2.8); I (2.4).

In particular, orthophosphorous acid or an ester of orthophosphorous acid may be used as compounds (component c)) which contain at least one phosphorus atom having the oxidation state +3. Esters of orthophosphorous acid are also referred to as phosphites. Orthophosphorous acid can also be present as a salt (generally as an alkali metal or ammonium salt). Preferred bonding partners of phosphorus are the elements C, S, O, N and/or H.

Phosphonites (esters of phosphonous acid), in particular those known as stabilizers, are also suitable.

Particularly suitable phosphites (i.e. the esters of orthophosphorous acid) and phosphonites (esters of phosphonous acid) include, for example, triphenyl phosphite, diphenyl alkyl phosphite, phenyl dialkyl phosphite tris(nonylphenyl) phosphite, trilauryl phosphite, trioctadecyl phosphite, distearyl pentaerythrityl, diphosphite, tris(2,4-di-tert-butylphenyl) phosphite, diisodecyl pentaerythrityl diphosphite, bis(2,4-di-tert-butylphenyl) pentaerythrityl diphosphite, bis(2,6-di-tert-butyl-4-methylphenyl) pentaerythrityl diphosphite, diisodecyloxypentaerythrityl diphosphite, bis(2,4-di-tert-butyl-6-methylphenyl) pentaerythrityl diphosphite, bis(2,4,6-tris(tert-butylphenyl)) pentaerythrityl diphosphite, tristearyl sorbityl triphosphite, tetrakis(2,4-di-tert-butyl-phenyl) 4,4'-biphenylene diphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocine, bis(2,4-di-tert-butyl-6-methylphenyl) methyl phosphite and bis(2,4-di-tert-butyl-6-methylphenyl) ethyl phosphite.

Esters of orthophosphorous acid (phosphites) of the formula (I) or esters of phosphonous acid (phosphonites) of the formula (II)

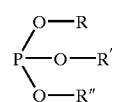  (I)

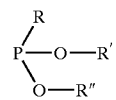  (II)

are advantageously used, where R, R' and R" may be identical or different and are organic radicals, in particular $C_1$–$C_{20}$-alkyl, hydroxy-$C_2$–$C_4$-alkyl, halo-$C_2$–$C_4$-alkyl, in particular chloroalkyl, $C_6$–$C_{10}$-aryl, in particular phenyl, or $C_1$–$C_8$-alkyl-substituted aryl (in particular $C_1$–$C_4$-alkyl-substituted phenyl). Furthermore, two of the three organic radicals R, R' and R", together with the phosphorus and the two oxygen atoms, may form a heterocyclic structure (for example having 5 or 6 atoms).

Trimethyl, triethyl, tributyl, trihexyl, trioctyl, triphenyl, tri-p-cresyl, trixylyl, tritolyl and tri-β-chloroethyl phosphite may be mentioned by name. However, dimethyl, diethyl, dibutyl, dioctyl, diphenyl, ditolyl and dixylyl phosphite are also inhibitors suitable according to the invention. Particularly suitable are the species known under the trade names Irgafos® 168 (producer Ciba AG), Irgafos® P-EPQ (producer Ciba AG) or Ultranox® 626 (producer GE-Speciality Chemicals GmbH):

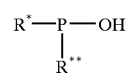  (III)

where R** is independent of R*, and R* and R** are each alkyl (preferably $C_1$- to $C_{20}$-alkyl) or aryl, in particular $C_6$–$C_{10}$-aryl (preferably phenyl).

Derivatives of the oxygen-containing phosphorus compounds described above which contain at least one phosphorus atom having the oxidation state +3 and in which one or more O atoms have been replaced by S or NR* (R* has the same meanings as those mentioned above) are also suitable.

In addition to one or more chemical compounds which contain at least one phosphorus atom having the oxidation state +3, the inhibitor composition according to the invention contains, inter alia, as further component (further inhibitor component), at least one nitroxyl radical (derivative) as component a).

A preferably used nitroxyl radical (derivative) is 4-hydroxy-1-oxyl-2,2,6,6-tetramethylpiperidine.

According to the invention, suitable nitroxyl radical (derivatives) (also referred to as N-oxyl radicals) are in principle all compounds which have at least one >N—O• group. The nitroxyl radical (derivatives) may also be produced in situ from other compounds, for example by H abstraction from hydroxylamines or by an addition reaction of C radicals with nitrones. However, they can also be produced in situ from aromatic amines which are derived from aniline or phenylenediamine. Nitroxyl radical (derivatives) suitable according to the invention are in particular those which are derived from a secondary amine

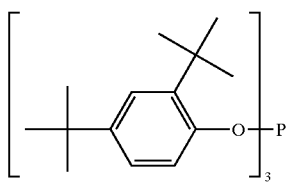

(Irgafos® 168)

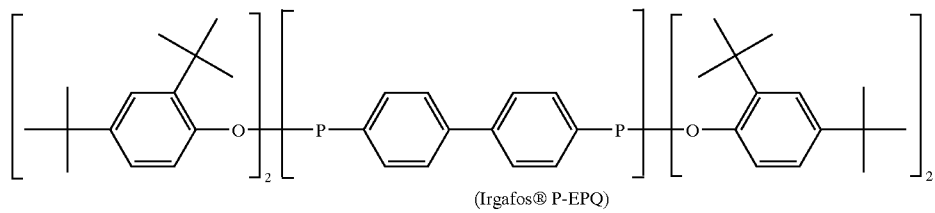

(Irgafos® P-EPQ)

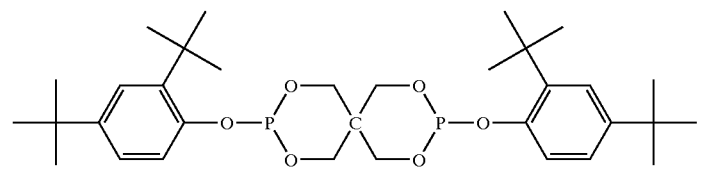

(Ultranox® 626)

Other suitable chemical compounds which contain at least one phosphorus atom which has the oxidation state +3 are the derivatives of phosphonous acid R*—P(OH)$_2$, where R* is alkyl (preferably $C_1$- to $C_8$-alkyl) or aryl, in particular $C_6$–$C_{10}$-aryl (preferably phenyl), and the derivatives of phosphonous acid of the formula (III)

which carries no hydrogen atoms on the α-carbon atoms (i.e. the N-oxyl groups are derived from corresponding secondary amino groups).

Such suitable, stable nitroxyl radical (derivatives) derived from a secondary amine are, for example, those of the formula (IV)

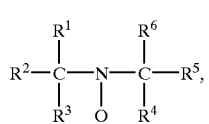
(IV)

where
R¹, R², R⁵ and R⁶ are identical or different straight-chain or branched, unsubstituted or substituted alkyl groups and
R³ and R⁴ are identical or different straight-chain or branched, unsubstituted or substituted alkyl groups or
R³CNCR⁴ is an unsubstituted or substituted cyclic structure.

Examples of suitable compounds are those stable nitroxyl radical (derivatives) of the formula (IV) in which R¹, R², R⁵ and R⁶ are (identical or different) $C_1$- to $C_4$-alkyl groups, such as methyl, ethyl, n-propyl, isopropyl, n-butyl, isobutyl or tert-butyl, linear or branched pentyl, phenyl or substituted groups thereof and R³ and R⁴ are (identical or different) $C_1$- to $C_4$-alkyl groups, such as methyl, ethyl, n-propyl, isopropyl, n-butyl, isobutyl or tert-butyl, linear or branched pentyl or substituted groups thereof or, together with CNC, are the cyclic structure

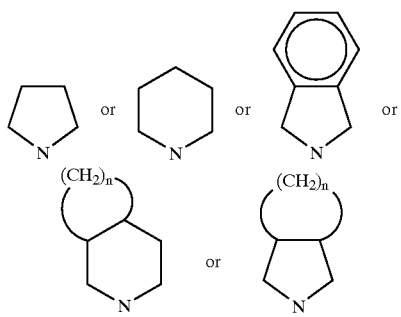

where n is an integer from 1 to 10 (frequently from 1 to 6), including substituted cyclic structures of this type. Typical examples are 2,2,6,6-tetramethyl-1-oxylpiperidine, 2,2,5,5-tetramethyl-1-oxylpyrrolidine and 4-oxo-2,2,6,6-tetramethyl-1-oxylpiperidine.

The N-oxyl radical (derivatives) of the formula (IV) can be prepared from the corresponding secondary amines by oxidation, for example with hydrogen peroxide. As a rule, they can be prepared as a pure substance.

The nitroxyl radical (derivatives) suitable according to the invention include in particular piperidin- or pyrrolidin-N-oxyls and di-N-oxyls of the following formulae (V) to (XII):

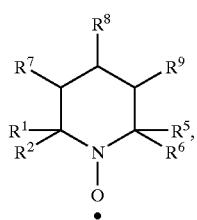
(V)

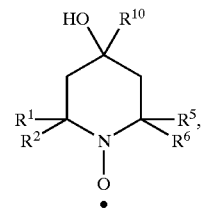
(VI)

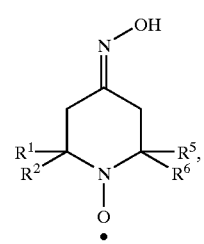
(VII)

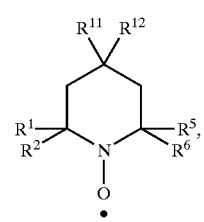
(VIII)

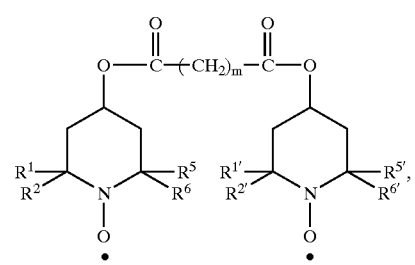
(IX)

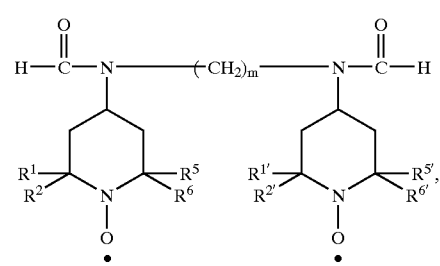
(X)

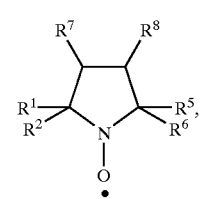
(XI)

-continued

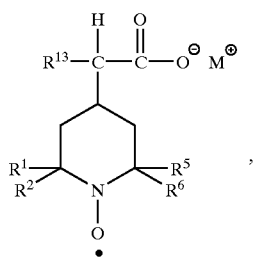
(XII)

where
m is from 2 to 10,
-$R^7$, -$R^8$ and -$R^9$, independently of one another, are each

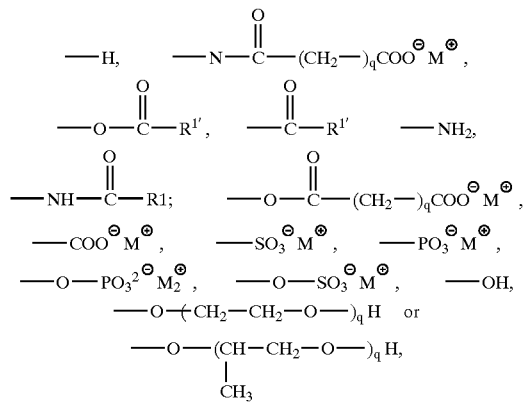

$M^\oplus$ is a hydrogen or an alkali metal ion,
q is an integer from 1 to 10,
$R^{1'}$, $R^{2'}$, $R^{5'}$ and $R^{6'}$, independently of one another and independently of $R^1$, $R^2$, $R^5$ and $R^6$, are the same groups as $R^1$,
$R^{10}$ is $C_1$- to $C_4$-alkyl, —CH=$CH_2$, —C≡CH, —CN,

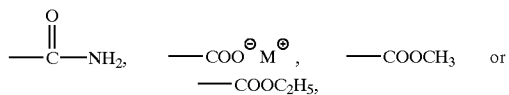

$R^{11}$ is an organic radical which has at least one primary, secondary (e.g. —$NHR^1$) or tertiary amino group (e.g. —$NR^1R^2$) or at least one ammonium group —$N^\oplus R^{14}R^{15}R^{16}X^U$, where $X^U$ is $F^U$, $Cl^U$, $Br^U$, $HSO_4^U$, $SO_4^{2U}$, $H_2PO_4^U$, $HPO_4^{2U}$ or $PO_4^{3U}$ and $R^{14}$, $R^{15}$ and $R^{16}$ are independent organic radicals (e.g. independently of one another and independently of $R^1$, the same groups as $R^1$), $R^{12}$, independently of $R^{11}$, has the same meanings as $R^{11}$ or is —H, —OH, $C_1$- to $C_4$-alkyl, $COO^U M^\oplus$, m—C≡CH,

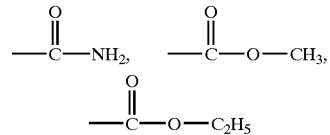

or hydroxyl-substituted $C_1$- to $C_4$-alkyl (e.g. hydroxyethyl or hydroxypropyl) or
$R^{11}$ and $R^{12}$ together are the oxygen of a carbonyl group and

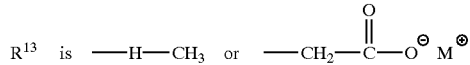

Preferably, $R^1=R^2=R^5=R^6=R^{1'}=R^{2'}=R^{5'}=R^{6'}$=—$CH_3$.

Typical examples of N-oxyl radical (derivatives) suitable according to the invention are 1-oxyl-2,2,6,6-tetramethylpiperidine, 1-oxyl-2,2,6,6-tetramethylpiperidin-4-ol, 1-oxyl-2,2,6,6-tetramethyl-4-methoxypiperidine, 1-oxyl-2,2,6,6-tetramethyl-4-ethoxypiperidine, 1-oxyl-2,2,6,6-tetramethyl-4-trimethylsilyloxypiperidine, 1-oxyl-2,2,6,6-tetramethyl-piperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl (4-tert-butyl)benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl)adipamide, N-(1-oxyl-2,2,6,6-tetramethylpiperidin-4-yl)caprolactam, N-(1-oxyl-2,2,6,6-tetramethylpiperidin-4-yl)dodecylsuccinimide, 2,4,6-tris[N-butyl-N-(1-oxyl-2,2,6,6-tetramethylpiperidin-4-yl]-s-triazine, N,N'-bis(1-oxyl-2,2,6,6-tetramethylpiperidin-4-yl)-N,N'-bisformyl-1,6-diaminohexane, 4,4'-ethylenebis(1-oxyl-2,2,6,6-tetramethylpiperazin-3-one) and tris(2,2,6,6-tetramethyl-1-oxylpiperidin-4-yl) phosphite and additionally 1-oxyl-2,2,6,6-tetramethyl-1,2,3,6-tetrahydropyridine.

Further suitable typical examples (in the corresponding structural formulae, H atoms are not shown) are:

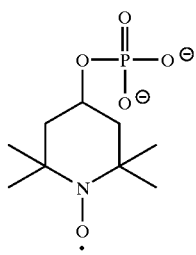

Sunamoto, Junzo; Akiyoshi, Kuzunari, Kihara, Tetsuji; Endo, Masayuki, BCS JA 8, Bull. Chem. Soc. Jpn., EN, 65, 4, 1992, pages 1041–1046;

-continued

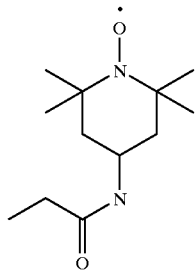
Beilstein Registry Number 6926369 ($C_{11}H_{22}N_3O_2$);

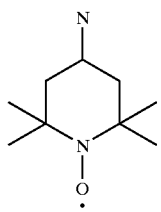
Beilstein Registry Number 6498805 (4-amino-2,2,6,6-tetramethyl-1-oxylpiperidine);

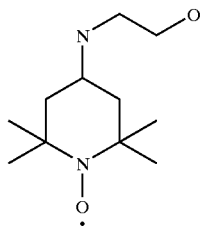
Beilstein Registry Number 6800244 ($C_{11}H_{23}N_2O_2$);

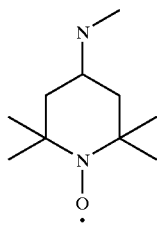
Beilstein Registry Number 5730772 (N-methyl-4-amino)-2,2,6,6-tetramethyl-1-oxyl-piperidine;

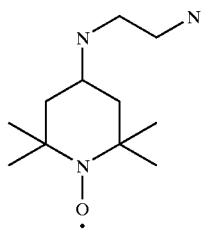
Beilstein Registry Number 5507538 (2,2,6,6-tetramethyl-4-(2-aminoethylamino)-1-oxyl-piperidine);

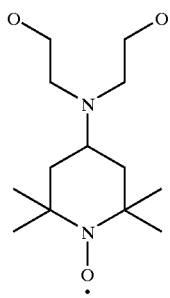
Beilstein Registry Number 4417950 (4<bis(2-hydroxyethyl)>amino-2,2,6,6-tetramethyl-1-oxyl-piperidine);

-continued

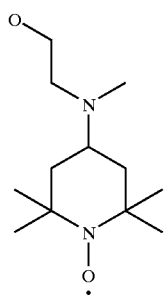 Beilstein Registry Number 4396625 ($C_{12}H_{25}N_2O_2$);

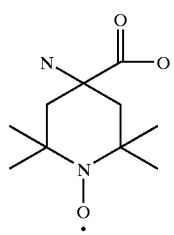 Beilstein Registry Number 4139900 (4-amino-2,2,6,6-tetramethyl-4-carboxyl-1-oxyl-piperidine);

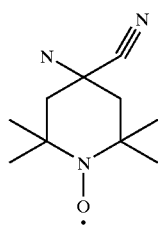 Beilstein Registry Number 4137088 (4-amino-4-cyano-2,2,6,6-tetramethyl-1-oxyl-piperidine);

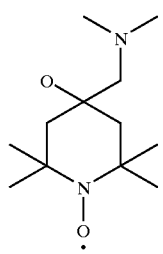 Beilstein Registry Number 3942714 ($C_{12}H_{25}N_2O_2$);

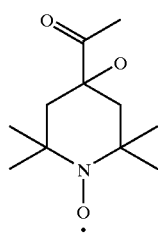 Beilstein Registry Number 1468515 (2,2,6,6-tetramethyl-4-hydroxy-4-acetyl-1-oxyl-piperidine);

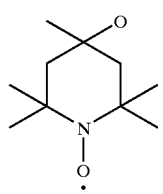 Beilstein Registry Number 1423410 (2,2,4,6,6-pentamethyl-4-hydroxy-1-oxyl-piperidine);

-continued

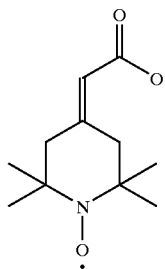
Beilstein Registry Number 6205316 (4-carboxymethylene-2,2,6,6-tetramethyl-1-oxyl-piperidine);

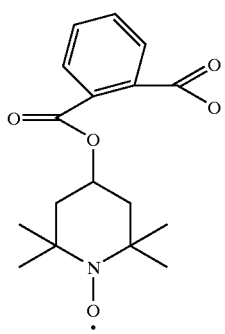
Beilstein Registry Number 1395538 (4-<2-carboxybenzoyloxy>-2,2,6,6-tetramethyl-1-oxylpiperidine);

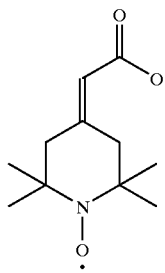
Beilstein Registry Number 3546230 (4-carboxymethyl-2,2,6,6-tetramethyl-1-oxyl-piperidine);

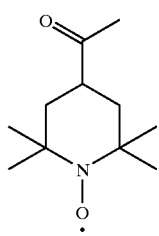
Beilstein Registry Number 3949026 (4-carboxyl-2,2,6,6-tetramethyl-1-oxyl-piperidine);

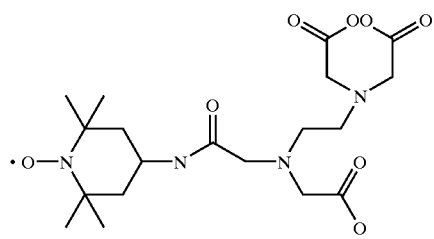
Beilstein Registry Number 4611003 N-mono(1-oxyl-2,2,6,6-tetramethylpiperidin-4-yl)ethylene-diaminetetraacetamide;

-continued
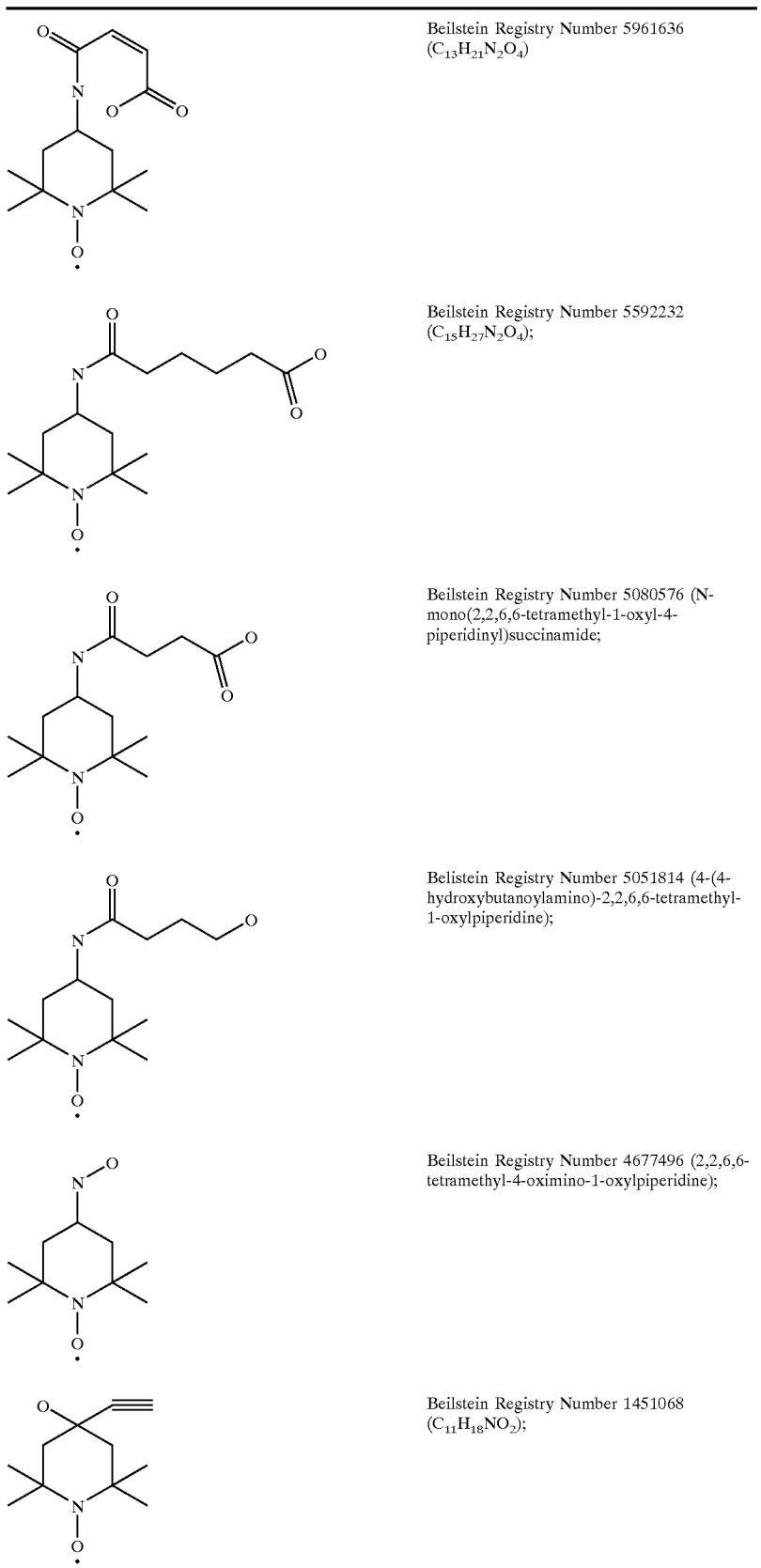
Beilstein Registry Number 5961636 ($C_{13}H_{21}N_2O_4$)
Beilstein Registry Number 5592232 ($C_{15}H_{27}N_2O_4$);
Beilstein Registry Number 5080576 (N-mono(2,2,6,6-tetramethyl-1-oxyl-4-piperidinyl)succinamide;
Belistein Registry Number 5051814 (4-(4-hydroxybutanoylamino)-2,2,6,6-tetramethyl-1-oxylpiperidine);
Beilstein Registry Number 4677496 (2,2,6,6-tetramethyl-4-oximino-1-oxylpiperidine);
Beilstein Registry Number 1451068 ($C_{11}H_{18}NO_2$);

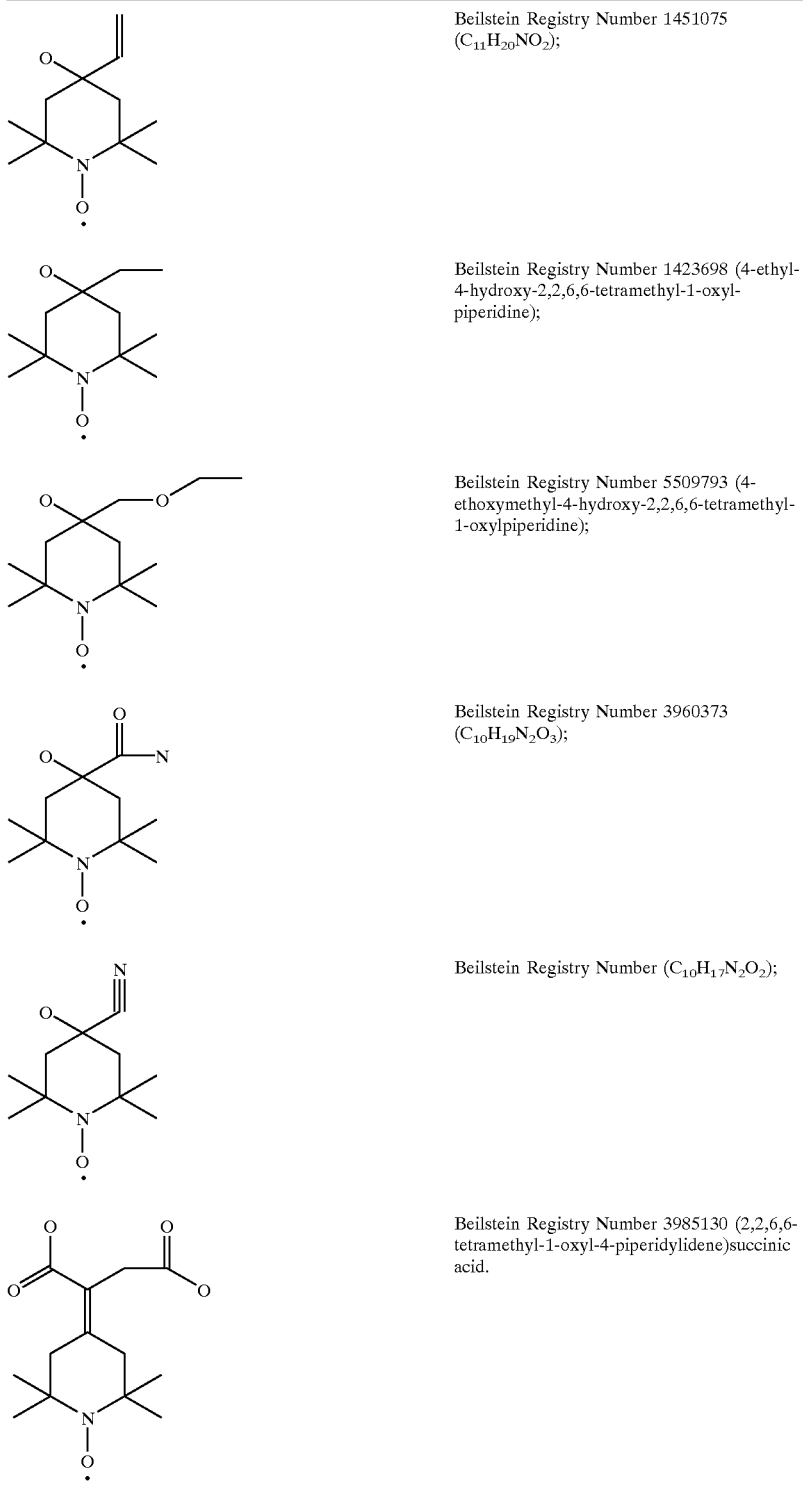

| | |
|---|---|
| | Beilstein Registry Number 1451075 ($C_{11}H_{20}NO_2$); |
| | Beilstein Registry Number 1423698 (4-ethyl-4-hydroxy-2,2,6,6-tetramethyl-1-oxyl-piperidine); |
| | Beilstein Registry Number 5509793 (4-ethoxymethyl-4-hydroxy-2,2,6,6-tetramethyl-1-oxylpiperidine); |
| | Beilstein Registry Number 3960373 ($C_{10}H_{19}N_2O_3$); |
| | Beilstein Registry Number ($C_{10}H_{17}N_2O_2$); |
| | Beilstein Registry Number 3985130 (2,2,6,6-tetramethyl-1-oxyl-4-piperidylidene)succinic acid. |

According to the invention, mixtures of N-oxyl radical (derivatives) can of course also be used.

The inhibitor composition also contains at least one phenol (derivative) (phenol as such is also suitable as phenol derivative) as a further component—component b). A preferably used phenol derivative is a phenol or cresol in which one or more hydrogen atoms have been substituted by tert-butyl groups, in particular 2,6-di-tert-butylcresol, or hydroquinones, in particular hydroquinone monomethyl ethers. Phenols or cresols in which one or more hydrogen atoms have been substituted by isopropyl groups, such as thymol or carvacrol, are also suitable. Pyrocatechol and its derivatives and resorcinol and its derivatives are also suitable. As described above, suitable dihydric phenols are also hydroquinone and its derivatives, in particular ethers of hydroquinone, such as hydroquinone monomethyl ether. Naphthols, such as α-naphthol and vitamin E are also suitable. Moreover, phenols which are linked to one another via alkyl bridges, such as bisphenol A, are also suitable. In general, suitable phenol derivatives are compounds which can form an oxyl radical which is bonded to an aromatic system. This is effected by homolytic cleavage of an oxygen-hydrogen bond, the oxygen atom being bonded to an aromatic system. Particularly preferred phenol derivatives are of the following structural formula (XIII):

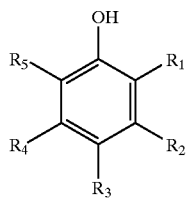

(XIII)

Here, $R_1$, $R_2$, $R_3$, R4 and $R_5$ are identical or different and are each H, halogen, $C_1$- to $C_{20}$-alkyl or aryl, $SO_3H$, $SO_3^-M^+$, OH, SH, O-alkyl, O-aryl, S-alkyl, S-aryl, NH-alkyl, NH-aryl, NO, $NO_2$, NH—OH, $NH_2$, COOH, CN, O—CO—$R_6$, O—CO—O—$R_6$, NH—CO—$R_6$, CN(—OH)—($R_6$), CO—O—$R_6$ or CO—NH—$R_6$, where $R_6$ is H, halogen, $C_1$- to $C_{20}$-alkyl or aryl, $SO_3H$, $SO_3^-M^+$, OH, SH, O-alkyl, O-aryl, S-alkyl, S-aryl, NH-alkyl, NH-aryl, NO, $NO_2$, NH—OH, $NH_2$, COOH or CN.

The inhibitor composition containing one or more chemical compounds which contain at least one phosphorus atom having the oxidation state +3, and one or more nitroxyl radical (derivatives) and one or more phenol (derivatives) has a particularly good stabilizing effect. Regarding the effect as inhibitor in free radical polymerization, the novel inhibitor composition has synergistic properties—species of the three different inhibitor components reinforce one another in their inhibiting effect. Accordingly, the inhibiting effect of the novel composition is better than the inhibiting effect which would be present, for example, in the presence of the individual components alone or as the sum of the individual effects.

It is advantageous that the novel inhibitor composition also displays its activity in the presence of molecular oxygen.

Particularly suitable inhibitor compositions are to be discussed below. Components which are contained in these inhibitor compositions are shown in the Table below—the combination of the following components proves particularly advantageous:

| Component a) | Component c) | Component b) |
|---|---|---|
| 4-Hydroxy-1-oxyl-2,2,6,6-tetramethylpiperidine | $P(OH)_3$ | 4-Tert-butylphenol |
| 4-Hydroxy-1-oxyl-2,2,6,6-tetramethylpiperidine | $P(Omethyl)_3$ | 4-Tert-butylphenol |
| 4-Hydroxy-1-oxyl-2,2,6,6-tetramethylpiperidine | $P(OEthyl)_3$ | 4-Tert-butylphenol |
| 4-Hydroxy-1-oxyl-2,2,6,6-tetramethylpiperidine | $P(Oiso\text{-}Propyl)_3$ | 4-Tert-butylphenol |
| 4-Hydroxy-1-oxyl-2,2,6,6-tetramethylpiperidine | $P(Opropyl)_3$ | 4-Tert-butylphenol |
| 4-Hydroxy-1-oxyl-2,2,6,6-tetramethylpiperidine | $P(On\text{-}Butyl)_3$ | 4-Tert-butylphenol |
| 4-Hydroxy-1-oxyl-2,2,6,6-tetramethylpiperidine | $P(Osec\text{-}Butyl)_3$ | 4-Tert-butylphenol |
| 4-Hydroxy-1-oxyl-2,2,6,6-tetramethylpiperidine | $P(Otert\text{-}Butyl)_3$ | 4-Tert-butylphenol |
| 4-Hydroxy-1-oxyl-2,2,6,6-tetramethylpiperidine | $P(OPhenyl)_3$ | 4-Tert-butylphenol |
| 4-Hydroxy-1-oxyl-2,2,6,6-tetramethylpiperidine | $P(OH)(OMethyl)_2$ | 4-Tert-butylphenol |
| 4-Hydroxy-1-oxyl-2,2,6,6-tetramethylpiperidine | $P(OH)(OEthyl)_2$ | 4-Tert-butylphenol |
| 4-Hydroxy-1-oxyl-2,2,6,6-tetramethylpiperidine | $P(OH)(Oiso\text{-}Propyl)_2$ | 4-Tert-butylphenol |
| 4-Hydroxy-1-oxyl-2,2,6,6-tetramethylpiperidine | $P(OH)(OPropyl)_2$ | 4-Tert-butylphenol |
| 4-Hydroxy-1-oxyl-2,2,6,6-tetramethylpiperidine | $P(OH)(On\text{-}Butyl)_2$ | 4-Tert-butylphenol |
| 4-Hydroxy-1-oxyl-2,2,6,6-tetramethylpiperidine | $P(OH)(Osec\text{-}Butyl)_2$ | 4-Tert-butylphenol |
| 4-Hydroxy-1-oxyl-2,2,6,6-tetramethylpiperidine | $P(OH)(Otert\text{-}Butyl)_2$ | 4-Tert-butylphenol |
| 4-Hydroxy-1-oxyl-2,2,6,6-tetramethylpiperidine | $P(OH)(OPhenyl)_2$ | 4-Tert-butylphenol |
| 4-Hydroxy-1-oxyl-2,2,6,6-tetramethylpiperidine | $P(OH)_2(OMethyl)$ | 4-Tert-butylphenol |
| 4-Hydroxy-1-oxyl-2,2,6,6-tetramethylpiperidine | $P(OH)_2(OEthyl)$ | 4-Tert-butylphenol |
| 4-Hydroxy-1-oxyl-2,2,6,6-tetramethylpiperidine | $P(OH)_2(Oiso\text{-}Propyl)$ | 4-Tert-butylphenol |
| 4-Hydroxy-1-oxyl-2,2,6,6-tetramethylpiperidine | $P(OH)_2(OPropyl)$ | 4-Tert-butylphenol |

-continued

| Component a) | Component c) | Component b) |
|---|---|---|
| 4-Hydroxy-1-oxyl-2,2,6,6-tetramethylpiperidine | P(OH)$_2$(On-Butyl) | 4-Tert-butylphenol |
| 4-Hydroxy-1-oxyl-2,2,6,6-tetramethylpiperidine | P(OH)$_2$(Osec-Butyl) | 4-Tert-butylphenol |
| 4-Hydroxy-1-oxyl-2,2,6,6-tetramethylpiperidine | P(OH)$_2$(Otert-Butyl) | 4-Tert-butylphenol |
| 4-Hydroxy-1-oxyl-2,2,6,6-tetramethylpiperidine | P(OH)$_2$(OPhenyl) | 4-Tert-butylphenol |
| 4-Hydroxy-1-oxyl-2,2,6,6-tetramethylpiperidine | (Methyl)P(OMethyl)$_2$ | 4-Tert-butylphenol |
| 4-Hydroxy-1-oxyl-2,2,6,6-tetramethylpiperidine | (Ethyl)P(OEthyl)$_2$ | 4-Tert-butylphenol |
| 4-Hydroxy-1-oxyl-2,2,6,6-tetramethylpiperidine | (iso-Propyl)P(Oiso-Propyl)$_2$ | 4-Tert-butylphenol |
| 4-Hydroxy-1-oxyl-2,2,6,6-tetramethylpiperidine | (Propyl)P(OPropyl)$_2$ | 4-Tert-butylphenol |
| 4-Hydroxy-1-oxyl-2,2,6,6-tetramethylpiperidine | (n-Butyl)P(On-Butyl)$_2$ | 4-Tert-butylphenol |
| 4-Hydroxy-1-oxyl-2,2,6,6-tetramethylpiperidine | (sec-Butyl)P(Osec-Butyl)$_2$ | 4-Tert-butylphenol |
| 4-Hydroxy-1-oxyl-2,2,6,6-tetramethylpiperidine | (tert-Butyl)P(Otert-Butyl)$_2$ | 4-Tert-butylphenol |
| 4-Hydroxy-1-oxyl-2,2,6,6-tetramethylpiperidine | (Phenyl)P(OPhenyl)$_2$ | 4-Tert-butylphenol |
| 4-Hydroxy-1-oxyl-2,2,6,6-tetramethylpiperidine | RP(OH)$_2$ | 4-Tert-butylphenol |
| 4-Hydroxy-1-oxyl-2,2,6,6-tetramethylpiperidine | RP(OH)(OR) | 4-Tert-butylphenol |
| where R = Me, Et, iso-Pr, n-Pr, n-Bu, sec-Bu, tert-Bu, phenyl | | |
| 4-Hydroxy-1-oxyl-2,2,6,6-tetramethylpiperidine | P(OH)$_3$ | 2,4-Di-tert-butylphenol |
| 4-Hydroxy-1-oxyl-2,2,6,6-tetramethylpiperidine | P(OMethyl)$_3$ | 2,4-Di-tert-butylphenol |
| 4-Hydroxy-1-oxyl-2,2,6,6-tetramethylpiperidine | P(OEthyl)$_3$ | 2,4-Di-tert-butylphenol |
| 4-Hydroxy-1-oxyl-2,2,6,6-tetramethylpiperidine | P(Oiso-Propyl)$_3$ | 2,4-Di-tert-butylphenol |
| 4-Hydroxy-1-oxyl-2,2,6,6-tetramethylpiperidine | P(OPropyl)$_3$ | 2,4-Di-tert-butylphenol |
| 4-Hydroxy-1-oxyl-2,2,6,6-tetramethylpiperidine | P(On-Butyl)$_3$ | 2,4-Di-tert-butylphenol |
| 4-Hydroxy-1-oxyl-2,2,6,6-tetramethylpiperidine | P(Osec-Butyl)$_3$ | 2,4-Di-tert-butylphenol |
| 4-Hydroxy-1-oxyl-2,2,6,6-tetramethylpiperidine | P(Otert-Butyl)$_3$ | 2,4-Di-tert-butylphenol |
| 4-Hydroxy-1-oxyl-2,2,6,6-tetramethylpiperidine | P(OPhenyl)$_3$ | 2,4-Di-tert-butylphenol |
| 4-Hydroxy-1-oxyl-2,2,6,6-tetramethylpiperidine | P(OH)(OMethyl)$_2$ | 2,4-Di-tert-butylphenol |
| 4-Hydroxy-1-oxyl-2,2,6,6-tetramethylpiperidine | P(OH)(OEthyl)$_2$ | 2,4-Di-tert-butylphenol |
| 4-Hydroxy-1-oxyl-2,2,6,6-tetramethylpiperidine | P(OH)(Oiso-Propyl)$_2$ | 2,4-Di-tert-butylphenol |
| 4-Hydroxy-1-oxyl-2,2,6,6-tetramethylpiperidine | P(OH)(OPropyl)$_2$ | 2,4-Di-tert-butylphenol |
| 4-Hydroxy-1-oxyl-2,2,6,6-tetramethylpiperidine | P(OH)(On-Butyl)$_2$ | 2,4-Di-tert-butylphenol |
| 4-Hydroxy-1-oxyl-2,2,6,6-tetramethylpiperidine | P(OH)(Osec-Butyl)$_2$ | 2,4-Di-tert-butylphenol |
| 4-Hydroxy-1-oxyl-2,2,6,6-tetramethylpiperidine | P(OH)(Otert-Butyl)$_2$ | 2,4-Di-tert-butylphenol |
| 4-Hydroxy-1-oxyl-2,2,6,6-tetramethylpiperidine | P(OH)(OPhenyl)$_2$ | 2,4-Di-tert-butylphenol |
| 4-Hydroxy-1-oxyl-2,2,6,6-tetramethylpiperidine | P(OH)$_2$(OMethyl) | 2,4-Di-tert-butylphenol |
| 4-Hydroxy-1-oxyl-2,2,6,6-tetramethylpiperidine | P(OH)$_2$(OEthyl) | 2,4-Di-tert-butylphenol |
| 4-Hydroxy-1-oxyl-2,2,6,6-tetramethylpiperidine | P(OH)$_2$(Oiso-Propyl) | 2,4-Di-tert-butylphenol |
| 4-Hydroxy-1-oxyl-2,2,6,6-tetramethylpiperidine | P(OH)$_2$(OPropyl) | 2,4-Di-tert-butylphenol |
| 4-Hydroxy-1-oxyl-2,2,6,6-tetramethylpiperidine | P(OH)$_2$(On-Butyl) | 2,4-Di-tert-butylphenol |
| 4-Hydroxy-1-oxyl-2,2,6,6-tetramethylpiperidine | P(OH)$_2$(Osec-Butyl) | 2,4-Di-tert-butylphenol |
| 4-Hydroxy-1-oxyl-2,2,6,6-tetramethylpiperidine | P(OH)$_2$(Otert-Butyl) | 2,4-Di-tert-butylphenol |

-continued

| Component a) | Component c) | Component b) |
|---|---|---|
| 4-Hydroxy-1-oxyl-2,2,6,6-tetramethylpiperidine | $P(OH)_2(OPhenyl)$ | 2,4-Di-tert-butylphenol |
| 4-Hydroxy-1-oxyl-2,2,6,6-tetramethylpiperidine | $(Methyl)P(OMethyl)_2$ | 2,4-Di-tert-butylphenol |
| 4-Hydroxy-1-oxyl-2,2,6,6-tetramethylpiperidine | $(Ethyl)P(OEthyl)_2$ | 2,4-Di-tert-butylphenol |
| 4-Hydroxy-1-oxyl-2,2,6,6-tetramethylpiperidine | $(iso\text{-}Propyl)P(Oiso\text{-}Propyl)_2$ | 2,4-Di-tert-butylphenol |
| 4-Hydroxy-1-oxyl-2,2,6,6-tetramethylpiperidine | $(Propyl)P(OPropyl)_2$ | 2,4-Di-tert-butylphenol |
| 4-Hydroxy-1-oxyl-2,2,6,6-tetramethylpiperidine | $(n\text{-}Butyl)P(On\text{-}Butyl)_2$ | 2,4-Di-tert-butylphenol |
| 4-Hydroxy-1-oxyl-2,2,6,6-tetramethylpiperidine | $(sec\text{-}Butyl)P(Osec\text{-}Butyl)_2$ | 2,4-Di-tert-butylphenol |
| 4-Hydroxy-1-oxyl-2,2,6,6-tetramethylpiperidine | $(tert\text{-}Butyl)P(Otert\text{-}Butyl)_2$ | 2,4-Di-tert-butylphenol |
| 4-Hydroxy-1-oxyl-2,2,6,6-tetramethylpiperidine | $(Phenyl)P(OPhenyl)_2$ | 2,4-Di-tert-butylphenol |
| 4-Hydroxy-1-oxyl-2,2,6,6-tetramethylpiperidine | $RP(OH)_2$ | 2,4-Di-tert-butylphenol |
| 4-Hydroxy-1-oxyl-2,2,6,6-tetramethylpiperidine | $RP(OH)(OR)$ | 2,4-Di-tert-butylphenol |
| where R = Me, Et, iso-Pr, n-Pr, n-Bu, sec-Bu, tert-Bu, phenyl | | |
| 4-Hydroxy-1-oxyl-2,2,6,6-tetramethylpiperidine | $P(OH)_3$ | Hydroquinone monomethyl ether |
| 4-Hydroxy-1-oxyl-2,2,6,6-tetramethylpiperidine | $P(OMethyl)_3$ | Hydroquinone monomethyl ether |
| 4-Hydroxy-1-oxyl-2,2,6,6-tetramethylpiperidine | $P(OEthyl)_3$ | Hydroquinone monomethyl ether |
| 4-Hydroxy-1-oxyl-2,2,6,6-tetramethylpiperidine | $P(Oiso\text{-}Propyl)_3$ | Hydroquinone monomethyl ether |
| 4-Hydroxy-1-oxyl-2,2,6,6-tetramethylpiperidine | $P(OPropyl)_3$ | Hydroquinone monomethyl ether |
| 4-Hydroxy-1-oxyl-2,2,6,6-tetramethylpiperidine | $P(On\text{-}Butyl)_3$ | Hydroquinone monomethyl ether |
| 4-Hydroxy-1-oxyl-2,2,6,6-tetramethylpiperidine | $P(Osec\text{-}Butyl)_3$ | Hydroquinone monomethyl ether |
| 4-Hydroxy-1-oxyl-2,2,6,6-tetramethylpiperidine | $P(Otert\text{-}Butyl)_3$ | Hydroquinone monomethyl ether |
| 4-Hydroxy-1-oxyl-2,2,6,6-tetramethylpiperidine | $P(OPhenyl)_3$ | Hydroquinone monomethyl ether |
| 4-Hydroxy-1-oxyl-2,2,6,6-tetramethylpiperidine | $P(OH)(OMethyl)_2$ | Hydroquinone monomethyl ether |
| 4-Hydroxy-1-oxyl-2,2,6,6-tetramethylpiperidine | $P(OH)(OEthyl)_2$ | Hydroquinone monomethyl ether |
| 4-Hydroxy-1-oxyl-2,2,6,6-tetramethylpiperidine | $P(OH)(Oiso\text{-}Propyl)_2$ | Hydroquinone monomethyl ether |
| 4-Hydroxy-1-oxyl-2,2,6,6-tetramethylpiperidine | $P(OH)(OPropyl)_2$ | Hydroquinone monomethyl ether |
| 4-Hydroxy-1-oxyl-2,2,6,6-tetramethylpiperidine | $P(OH)(On\text{-}Butyl)_2$ | Hydroquinone monomethyl ether |
| 4-Hydroxy-1-oxyl-2,2,6,6-tetramethylpiperidine | $P(OH)(Osec\text{-}Butyl)_2$ | Hydroquinone monomethyl ether |
| 4-Hydroxy-1-oxyl-2,2,6,6-tetramethylpiperidine | $P(OH)(Otert\text{-}Butyl)_2$ | Hydroquinone monomethyl ether |
| 4-Hydroxy-1-oxyl-2,2,6,6-tetramethylpiperidine | $P(OH)(OPhenyl)_2$ | Hydroquinone monomethyl ether |
| 4-Hydroxy-1-oxyl-2,2,6,6-tetramethylpiperidine | $P(OH)_2(OMethyl)$ | Hydroquinone monomethyl ether |
| 4-Hydroxy-1-oxyl-2,2,6,6-tetramethylpiperidine | $P(OH)_2(OEthyl)$ | Hydroquinone monomethyl ether |
| 4-Hydroxy-1-oxyl-2,2,6,6-tetramethylpiperidine | $P(OH)_2(Oiso\text{-}Propyl)$ | Hydroquinone monomethyl ether |
| 4-Hydroxy-1-oxyl-2,2,6,6-tetramethylpiperidine | $P(OH)_2(OPropyl)$ | Hydroquinone monomethyl ether |
| 4-Hydroxy-1-oxyl-2,2,6,6-tetramethylpiperidine | $P(OH)_2(On\text{-}Butyl)$ | Hydroquinone monomethyl ether |
| 4-Hydroxy-1-oxyl-2,2,6,6-tetramethylpiperidine | $P(OH)_2(Osec\text{-}Butyl)$ | Hydroquinone monomethyl ether |
| 4-Hydroxy-1-oxyl-2,2,6,6-tetramethylpiperidine | $P(OH)_2(Otert\text{-}Butyl)$ | Hydroquinone monomethyl ether |
| 4-Hydroxy-1-oxyl-2,2,6,6-tetramethylpiperidine | $P(OH)_2(OPhenyl)$ | Hydroquinone monomethyl ether |
| 4-Hydroxy-1-oxyl-2,2,6,6-tetramethylpiperidine | $(Methyl)P(OMethyl)_2$ | Hydroquinone monomethyl ether |
| 4-Hydroxy-1-oxyl-2,2,6,6-tetramethylpiperidine | $(Ethyl)P(OEthyl)_2$ | Hydroquinone monomethyl ether |

-continued

| Component a) | Component c) | Component b) |
|---|---|---|
| 4-Hydroxy-1-oxyl-2,2,6,6-tetramethylpiperidine | (iso-Propyl)P(Oiso-Propyl)$_2$ | Hydroquinone monomethyl ether |
| 4-Hydroxy-1-oxyl-2,2,6,6-tetramethylpiperidine | (Propyl)P(OPropyl)$_2$ | Hydroquinone monomethyl ether |
| 4-Hydroxy-1-oxyl-2,2,6,6-tetramethylpiperidine | (n-Butyl)P(On-Butyl)$_2$ | Hydroquinone monomethyl ether |
| 4-Hydroxy-1-oxyl-2,2,6,6-tetramethylpiperidine | (sec-Butyl)P(Osec-Butyl)$_2$ | Hydroquinone monomethyl ether |
| 4-Hydroxy-1-oxyl-2,2,6,6-tetramethylpiperidine | (tert-Butyl)P(Otert-Butyl)$_2$ | Hydroquinone monomethyl ether |
| 4-Hydroxy-1-oxyl-2,2,6,6-tetramethylpiperidine | (Phenyl)P(OPhenyl)$_2$ | Hydroquinone monomethyl ether |
| 4-Hydroxy-1-oxyl-2,2,6,6-tetramethylpiperidine | RP(OH)$_2$ | Hydroquinone monomethyl ether |
| 4-Hydroxy-1-oxyl-2,2,6,6-tetramethylpiperidine | RP(OH)(OR) | Hydroquinone monomethyl ether |
| where R = Me, Et, iso-Pr, n-Pr, n-Bu, sec-Bu, tert-Bu, phenyl | | |
| 4-Hydroxy-1-oxyl-2,2,6,6-tetramethylpiperidine | P(OH)$_3$ | Phenol |
| 4-Hydroxy-1-oxyl-2,2,6,6-tetramethylpiperidine | P(OMethyl)$_3$ | Phenol |
| 4-Hydroxy-1-oxyl-2,2,6,6-tetramethylpiperidine | P(OEthyl)$_3$ | Phenol |
| 4-Hydroxy-1-oxyl-2,2,6,6-tetramethylpiperidine | P(Oiso-Propyl)$_3$ | Phenol |
| 4-Hydroxy-1-oxyl-2,2,6,6-tetramethylpiperidine | P(OPropyl)$_3$ | Phenol |
| 4-Hydroxy-1-oxyl-2,2,6,6-tetramethylpiperidine | P(On-Butyl)$_3$ | Phenol |
| 4-Hydroxy-1-oxyl-2,2,6,6-tetramethylpiperidine | P(Osec-Butyl)$_3$ | Phenol |
| 4-Hydroxy-1-oxyl-2,2,6,6-tetramethylpiperidine | P(Otert-Butyl)$_3$ | Phenol |
| 4-Hydroxy-1-oxyl-2,2,6,6-tetramethylpiperidine | P(OPhenyl)$_3$ | Phenol |
| 4-Hydroxy-1-oxyl-2,2,6,6-tetramethylpiperidine | P(OH)(OMethyl)$_2$ | Phenol |
| 4-Hydroxy-1-oxyl-2,2,6,6-tetramethylpiperidine | P(OH)(OEthyl)$_2$ | Phenol |
| 4-Hydroxy-1-oxyl-2,2,6,6-tetramethylpiperidine | P(OH)(Oiso-Propyl)$_2$ | Phenol |
| 4-Hydroxy-1-oxyl-2,2,6,6-tetramethylpiperidine | P(OH)(OPropyl)$_2$ | Phenol |
| 4-Hydroxy-1-oxyl-2,2,6,6-tetramethylpiperidine | P(OH)(On-Butyl)$_2$ | Phenol |
| 4-Hydroxy-1-oxyl-2,2,6,6-tetramethylpiperidine | P(OH)(Osec-Butyl)$_2$ | Phenol |
| 4-Hydroxy-1-oxyl-2,2,6,6-tetramethylpiperidine | P(OH)(Otert-Butyl)$_2$ | Phenol |
| 4-Hydroxy-1-oxyl-2,2,6,6-tetramethylpiperidine | P(OH)(OPhenyl)$_2$ | Phenol |
| 4-Hydroxy-1-oxyl-2,2,6,6-tetramethylpiperidine | P(OH)$_2$(OMethyl) | Phenol |
| 4-Hydroxy-1-oxyl-2,2,6,6-tetramethylpiperidine | P(OH)$_2$(OEthyl) | Phenol |
| 4-Hydroxy-1-oxyl-2,2,6,6-tetramethylpiperidine | P(OH)$_2$(Oiso-Propyl) | Phenol |
| 4-Hydroxy-1-oxyl-2,2,6,6-tetramethylpiperidine | P(OH)$_2$(OPropyl) | Phenol |
| 4-Hydroxy-1-oxyl-2,2,6,6-tetramethylpiperidine | P(OH)$_2$(On-Butyl) | Phenol |
| 4-Hydroxy-1-oxyl-2,2,6,6-tetramethylpiperidine | P(OH)$_2$(Osec-Butyl) | Phenol |
| 4-Hydroxy-1-oxyl-2,2,6,6-tetramethylpiperidine | P(OH)$_2$(Otert-Butyl) | Phenol |
| 4-Hydroxy-1-oxyl-2,2,6,6-tetramethylpiperidine | P(OH)$_2$(OPhenyl) | Phenol |
| 4-Hydroxy-1-oxyl-2,2,6,6-tetramethylpiperidine | (Methyl)P(OMethyl)$_2$ | Phenol |
| 4-Hydroxy-1-oxyl-2,2,6,6-tetramethylpiperidine | (Ethyl)P(OEthyl)$_2$ | Phenol |
| 4-Hydroxy-1-oxyl-2,2,6,6-tetramethylpiperidine | (iso-Propyl)P(Oiso-Propyl)$_2$ | Phenol |
| 4-Hydroxy-1-oxyl-2,2,6,6-tetramethylpiperidine | (Propyl)P(OPropyl)$_2$ | Phenol |
| 4-Hydroxy-1-oxyl-2,2,6,6-tetramethylpiperidine | (n-Butyl)P(On-Butyl)$_2$ | Phenol |

-continued

| Component a) | Component c) | Component b) |
|---|---|---|
| 4-Hydroxy-1-oxyl-2,2,6,6-tetramethylpiperidine | (sec-Butyl)P(Osec-Butyl)$_2$ | Phenol |
| 4-Hydroxy-1-oxyl-2,2,6,6-tetramethylpiperidine | (tert-Butyl)P(Otert-Butyl)$_2$ | Phenol |
| 4-Hydroxy-1-oxyl-2,2,6,6-tetramethylpiperidine | (Phenyl)P(OPhenyl)$_2$ | Phenol |
| 4-Hydroxy-1-oxyl-2,2,6,6-tetramethylpiperidine | RP(OH)$_2$ | Phenol |
| 4-Hydroxy-1-oxyl-2,2,6,6-tetramethylpiperidine | RP(OH)(OR) | Phenol |
| where R = Me, Et, iso-Pr, n-Pr, n-Bu, sec-Bu, tert-Bu, phenyl | | |
| 4-Hydroxy-1-oxyl-2,2,6,6-tetramethylpiperidine | P(OH)$_3$ | Tert-butylpyrocatechol |
| 4-Hydroxy-1-oxyl-2,2,6,6-tetramethylpiperidine | P(OMethyl)$_3$ | Tert-butylpyrocatechol |
| 4-Hydroxy-1-oxyl-2,2,6,6-tetramethylpiperidine | P(OEthyl)$_3$ | Tert-butylpyrocatechol |
| 4-Hydroxy-1-oxyl-2,2,6,6-tetramethylpiperidine | P(Oiso-Propyl)$_3$ | Tert-butylpyrocatechol |
| 4-Hydroxy-1-oxyl-2,2,6,6-tetramethylpiperidine | P(OPropyl)$_3$ | Tert-butylpyrocatechol |
| 4-Hydroxy-1-oxyl-2,2,6,6-tetramethylpiperidine | P(On-Butyl)$_3$ | Tert-butylpyrocatechol |
| 4-Hydroxy-1-oxyl-2,2,6,6-tetramethylpiperidine | P(Osec-Butyl)$_3$ | Tert-butylpyrocatechol |
| 4-Hydroxy-1-oxyl-2,2,6,6-tetramethylpiperidine | P(Otert-Butyl)$_3$ | Tert-butylpyrocatechol |
| 4-Hydroxy-1-oxyl-2,2,6,6-tetramethylpiperidine | P(OPhenyl)$_3$ | Tert-butylpyrocatechol |
| 4-Hydroxy-1-oxyl-2,2,6,6-tetramethylpiperidine | P(OH)(OMethyl)$_2$ | Tert-butylpyrocatechol |
| 4-Hydroxy-1-oxyl-2,2,6,6-tetramethylpiperidine | P(OH)(OEthyl)$_2$ | Tert-butylpyrocatechol |
| 4-Hydroxy-1-oxyl-2,2,6,6-tetramethylpiperidine | P(OH)(Oiso-Propyl)$_2$ | Tert-butylpyrocatechol |
| 4-Hydroxy-1-oxyl-2,2,6,6-tetramethylpiperidine | P(OH)(OPropyl)$_2$ | Tert-butylpyrocatechol |
| 4-Hydroxy-1-oxyl-2,2,6,6-tetramethylpiperidine | P(OH)(On-Butyl)$_2$ | Tert-butylpyrocatechol |
| 4-Hydroxy-1-oxyl-2,2,6,6-tetramethylpiperidine | P(OH)(Osec-Butyl)$_2$ | Tert-butylpyrocatechol |
| 4-Hydroxy-1-oxyl-2,2,6,6-tetramethylpiperidine | P(OH)(Otert-Butyl)$_2$ | Tert-butylpyrocatechol |
| 4-Hydroxy-1-oxyl-2,2,6,6-tetramethylpiperidine | P(OH)(OPhenyl)$_2$ | Tert-butylpyrocatechol |
| 4-Hydroxy-1-oxyl-2,2,6,6-tetramethylpiperidine | P(OH)$_2$(OMethyl) | Tert-butylpyrocatechol |
| 4-Hydroxy-1-oxyl-2,2,6,6-tetramethylpiperidine | P(OH)$_2$(OEthyl) | Tert-butylpyrocatechol |
| 4-Hydroxy-1-oxyl-2,2,6,6-tetramethylpiperidine | P(OH)$_2$(Oiso-Propyl) | Tert-butylpyrocatechol |
| 4-Hydroxy-1-oxyl-2,2,6,6-tetramethylpiperidine | P(OH)$_2$(OPropyl) | Tert-butylpyrocatechol |
| 4-Hydroxy-1-oxyl-2,2,6,6-tetramethylpiperidine | P(OH)$_2$(On-Butyl) | Tert-butylpyrocatechol |
| 4-Hydroxy-1-oxyl-2,2,6,6-tetramethylpiperidine | P(OH)$_2$(Osec-Butyl) | Tert-butylpyrocatechol |
| 4-Hydroxy-1-oxyl-2,2,6,6-tetramethylpiperidine | P(OH)$_2$(Otert-Butyl) | Tert-butylpyrocatechol |
| 4-Hydroxy-1-oxyl-2,2,6,6-tetramethylpiperidine | P(OH)$_2$(OPhenyl) | Tert-butylpyrocatechol |
| 4-Hydroxy-1-oxyl-2,2,6,6-tetramethylpiperidine | (Methyl)P(OMethyl)$_2$ | Tert-butylpyrocatechol |
| 4-Hydroxy-1-oxyl-2,2,6,6-tetramethylpiperidine | (Ethyl)P(OEthyl)$_2$ | Tert-butylpyrocatechol |
| 4-Hydroxy-1-oxyl-2,2,6,6-tetramethylpiperidine | (iso-Propyl)P(Oiso-Propyl)$_2$ | Tert-butylpyrocatechol |
| 4-Hydroxy-1-oxyl-2,2,6,6-tetramethylpiperidine | (Propyl)P(OPropyl)$_2$ | Tert-butylpyrocatechol |
| 4-Hydroxy-1-oxyl-2,2,6,6-tetramethylpiperidine | (n-Butyl)P(On-Butyl)$_2$ | Tert-butylpyrocatechol |
| 4-Hydroxy-1-oxyl-2,2,6,6-tetramethylpiperidine | (sec-Butyl)P(Osec-Butyl)$_2$ | Tert-butylpyrocatechol |
| 4-Hydroxy-1-oxyl-2,2,6,6-tetramethylpiperidine | (tert-Butyl)P(Otert-Butyl)$_2$ | Tert-butylpyrocatechol |
| 4-Hydroxy-1-oxyl-2,2,6,6-tetramethylpiperidine | (Phenyl)P(OPhenyl)$_2$ | Tert-butylpyrocatechol |

-continued

| Component a) | Component c) | Component b) |
|---|---|---|
| 4-Hydroxy-1-oxyl-2,2,6,6-tetramethylpiperidine | RP(OH)$_2$ | Tert-butylpyrocatechol |
| 4-Hydroxy-1-oxyl-2,2,6,6-tetramethylpiperidine | RP(OH)(OR) | Tert-butylpyrocatechol |
| where R = Me, Et, iso-Pr, n-Pr, n-Bu, sec-Bu, tert-Bu, phenyl | | |
| 4-Hydroxy-1-oxyl-2,2,6,6-tetramethylpiperidine | P(OH)$_3$ | 2,6-Tert-butyl-4-methylphenol |
| 4-Hydroxy-1-oxyl-2,2,6,6-tetramethylpiperidine | P(OMethyl)$_3$ | 2,6-Tert-butyl-4-methylphenol |
| 4-Hydroxy-1-oxyl-2,2,6,6-tetramethylpiperidine | P(OEthyl)$_3$ | 2,6-Tert-butyl-4-methylphenol |
| 4-Hydroxy-1-oxyl-2,2,6,6-tetramethylpiperidine | P(Oiso-Propyl)$_3$ | 2,6-Tert-butyl-4-methylphenol |
| 4-Hydroxy-1-oxyl-2,2,6,6-tetramethylpiperidine | P(OPropyl)$_3$ | 2,6-Tert-butyl-4-methylphenol |
| 4-Hydroxy-1-oxyl-2,2,6,6-tetramethylpiperidine | P(On-Butyl)$_3$ | 2,6-Tert-butyl-4-methylphenol |
| 4-Hydroxy-1-oxyl-2,2,6,6-tetramethylpiperidine | P(Osec-Butyl)$_3$ | 2,6-Tert-butyl-4-methylphenol |
| 4-Hydroxy-1-oxyl-2,2,6,6-tetramethylpiperidine | P(Otert-Butyl)$_3$ | 2,6-Tert-butyl-4-methylphenol |
| 4-Hydroxy-1-oxyl-2,2,6,6-tetramethylpiperidine | P(OPhenyl)$_3$ | 2,6-Tert-butyl-4-methylphenol |
| 4-Hydroxy-1-oxyl-2,2,6,6-tetramethylpiperidine | P(OH)(OMethyl)$_2$ | 2,6-Tert-butyl-4-methylphenol |
| 4-Hydroxy-1-oxyl-2,2,6,6-tetramethylpiperidine | P(OH)(OEthyl)$_2$ | 2,6-Tert-butyl-4-methylphenol |
| 4-Hydroxy-1-oxyl-2,2,6,6-tetramethylpiperidine | P(OH)(Oiso-Propyl)$_2$ | 2,6-Tert-butyl-4-methylphenol |
| 4-Hydroxy-1-oxyl-2,2,6,6-tetramethylpiperidine | P(OH)(OPropyl)$_2$ | 2,6-Tert-butyl-4-methylphenol |
| 4-Hydroxy-1-oxyl-2,2,6,6-tetramethylpiperidine | P(OH)(On-Butyl)$_2$ | 2,6-Tert-butyl-4-methylphenol |
| 4-Hydroxy-1-oxyl-2,2,6,6-tetramethylpiperidine | P(OH)(Osec-Butyl)$_2$ | 2,6-Tert-butyl-4-methylphenol |
| 4-Hydroxy-1-oxyl-2,2,6,6-tetramethylpiperidine | P(OH)(Otert-Butyl)$_2$ | 2,6-Tert-butyl-4-methylphenol |
| 4-Hydroxy-1-oxyl-2,2,6,6-tetramethylpiperidine | P(OH)(OPhenyl)$_2$ | 2,6-Tert-butyl-4-methylphenol |
| 4-Hydroxy-1-oxyl-2,2,6,6-tetramethylpiperidine | P(OH)$_2$(OMethyl) | 2,6-Tert-butyl-4-methylphenol |
| 4-Hydroxy-1-oxyl-2,2,6,6-tetramethylpiperidine | P(OH)$_2$(OEthyl) | 2,6-Tert-butyl-4-methylphenol |
| 4-Hydroxy-1-oxyl-2,2,6,6-tetramethylpiperidine | P(OH)$_2$(Oiso-Propyl) | 2,6-Tert-butyl-4-methylphenol |
| 4-Hydroxy-1-oxyl-2,2,6,6-tetramethylpiperidine | P(OH)$_2$(OPropyl) | 2,6-Tert-butyl-4-methylphenol |
| 4-Hydroxy-1-oxyl-2,2,6,6-tetramethylpiperidine | P(OH)$_2$(On-Butyl) | 2,6-Tert-butyl-4-methylphenol |
| 4-Hydroxy-1-oxyl-2,2,6,6-tetramethylpiperidine | P(OH)$_2$(Osec-Butyl) | 2,6-Tert-butyl-4-methylphenol |
| 4-Hydroxy-1-oxyl-2,2,6,6-tetramethylpiperidine | P(OH)$_2$(Otert-Butyl) | 2,6-Tert-butyl-4-methylphenol |
| 4-Hydroxy-1-oxyl-2,2,6,6-tetramethylpiperidine | P(OH)$_2$(OPhenyl) | 2,6-Tert-butyl-4-methylphenol |
| 4-Hydroxy-1-oxyl-2,2,6,6-tetramethylpiperidine | (Methyl)P(OMethyl)$_2$ | 2,6-Tert-butyl-4-methylphenol |
| 4-Hydroxy-1-oxyl-2,2,6,6-tetramethylpiperidine | (Ethyl)P(OEthyl)$_2$ | 2,6-Tert-butyl-4-methylphenol |
| 4-Hydroxy-1-oxyl-2,2,6,6-tetramethylpiperidine | (iso-Propyl)P(Oiso-Propyl)$_2$ | 2,6-Tert-butyl-4-methylphenol |
| 4-Hydroxy-1-oxyl-2,2,6,6-tetramethylpiperidine | (Propyl)P(OPropyl)$_2$ | 2,6-Tert-butyl-4-methylphenol |
| 4-Hydroxy-1-oxyl-2,2,6,6-tetramethylpiperidine | (n-Butyl)P(On-Butyl)$_2$ | 2,6-Tert-butyl-4-methylphenol |
| 4-Hydroxy-1-oxyl-2,2,6,6-tetramethylpiperidine | (sec-Butyl)P(Osec-Butyl)$_2$ | 2,6-Tert-butyl-4-methylphenol |
| 4-Hydroxy-1-oxyl-2,2,6,6-tetramethylpiperidine | (tert-Butyl)P(Otert-Butyl)$_2$ | 2,6-Tert-butyl-4-methylphenol |
| 4-Hydroxy-1-oxyl-2,2,6,6-tetramethylpiperidine | (Phenyl)P(OPhenyl)$_2$ | 2,6-Tert-butyl-4-methylphenol |
| 4-Hydroxy-1-oxyl-2,2,6,6-tetramethylpiperidine | RP(OH)$_2$ | 2,6-Tert-butyl-4-methylphenol |
| 4-Hydroxy-1-oxyl-2,2,6,6-tetramethylpiperidine | RP(OH)(OR) | 2,6-Tert-butyl-4-methylphenol |
| where R = Me, Et, iso-Pr, n-Pr, n-Bu, sec-Bu, tert-Bu, phenyl | | |

The particular advantage of the novel inhibitor composition—the "three-component combination"—is that overall only a small amount of inhibitor is required.

In rectification and distillation processes, comparatively less polymer is deposited if the novel inhibitor system is used, so that the corresponding plants have to be shut down less frequently for cleaning work. Moreover, the inhibitor system having a synergistic effect ensures that a smaller amount of monomer is consumed by polymerization and thus lost.

Of course, the inhibitor composition may also contain further components inhibiting free radical polymerization, in addition to the inhibitors described—phosphorus compounds, nitroxyl radical (derivatives) and phenol (derivatives). Examples of such other free radical polymerization inhibitors are organic nitroso compounds, such as N-nitrosoarylamines. These inhibitor compositions also have activity in the presence of molecular oxygen.

The inhibitor compositions are used in accordance with the invention for the stabilization of pure substances which have at least one vinylically unsaturated group or of mixtures which contain at least one substance which has at least one vinylically unsaturated group. The inhibitor composition is also effected in the presence of oxygen.

According to the invention, a mixture containing at least one compound which has at least one vinylically unsaturated group and a novel inhibitor composition is also provided.

The mixture contains, as a rule, one or more chemical compounds which contain at least one phosphorus atom having the oxidation state +3, in a total concentration of from 1 to 5000 ppm, preferably from 5 to 1000 ppm, and one or more nitroxyl radical (derivatives) in a total concentration of from 1 to 3000 ppm, preferably from 5 to 300 ppm, and one or more phenol derivatives in a total concentration of from 1 to 3000 ppm, preferably from 5 to 1500 ppm.

Compounds which have at least one vinylically unsaturated group are to be understood as meaning in particular those capable of free radical homo- and/or copolymerization. These are, for example, olefins, such as isobutene, ethylene or propylene, vinylaromatic monomers, such as styrene, α-methylstyrene, o-chlorostyrene or vinyltoluenes, conjugated $C_4$–$C_8$-dienes, such as butadiene or isoprene, and esters of vinyl alcohol and monocarboxylic acids of 1 to 18 carbon atoms, such as vinyl acetate, vinyl propionate, vinyl n-butyrate, vinyl laurate or vinyl stearate. In particular, α,β-monoethylenically unsaturated mono- and dicarboxylic acids of 3 to 6 carbon atoms, especially acrylic acid, methacrylic acid, maleic acid, fumaric acid and itaconic acid, the esters of the abovementioned carboxylic acids and alkanols of 1 to 12, preferably 1 to 4, carbon atoms, in particular methyl, ethyl, n-butyl, isobutyl, tert-butyl and 2-ethylhexyl acrylate and methacrylate, dimethyl maleate or di-n-butyl maleate, are also suitable.

However, precursor aldehydes, nitriles and amides of the abovementioned α,β-monoethylenically unsaturated mono- and dicarboxylic acids of 3 to 6 carbon atoms, for example acrolein, methacrolein, acrylonitrile, methacrylonitrile, acrylamide and methacrylamide, are also suitable. Monomers, such as vinylsulfonic acid, vinylphosphonic acid, N-vinylimidazole and N-vinylpyrrolidone, are also suitable.

The novel inhibitor composition is suitable as an additive both for stabilization during storage and for process stabilization (preparation, purification and chemical reaction) of at least one vinylically unsaturated group. The latter also applies in particular to distillation processes, which as a rule take place at from 50 to 300° C., preferably from 50 to 200° C., particularly preferably from 50 to 150° C.

Stabilization using the novel inhibitor composition is particularly suitable in the case of the distillation (rectification) of (meth)acrylic esters (in particular the abovementioned typical examples), during their separation by distillation or rectification from product mixtures such as those which result from acid-catalyzed esterification of (meth)acrylic acid with alcohols, in particular alkanols (especially $C_1$- to $C_{12}$- or $C_1$- to $C_8$-alkanols), before and/or after removal of the acid catalyst.

However, said inhibitor composition is also suitable for stabilizing the abovementioned (meth)acrylic ester-containing mixtures which contain neither esterification catalyst nor acrylic acid nor methacrylic acid itself. Such (meth)acrylic ester-containing mixtures are formed, for example, by the abovementioned esterification product mixtures after, for example removal of the acid catalyst by extraction and/or rectification and after appropriate removal of the excess (meth)acrylic acid.

A (meth)acrylic ester-containing mixture subjected to distillation or rectification can be stabilized by adding the inhibitors to the mixture before the distillation.

In addition, stabilization can be effected by adding an inhibitor at the top of the column. Of course, the entire stabilization may also be effected exclusively by adding an inhibitor at the top of the column.

The various components of the novel inhibitor composition may be added in succession simultaneously or in premixed form. The abovementioned also applies to the other inhibitors if the inhibitor composition comprises them.

The components of the inhibitor composition may also be added at different feed points. For example, components of the inhibitor system can be added at the top of the rectification column and other components of the inhibitor system can be added at the bottom and/or to the feed of the rectification column. This applies both to those rectifications in the course of which the (meth)acrylic ester is isolated via a top takeoff, via a bottom takeoff and/or via a side takeoff. In the case of continuous isolation of (meth)acrylic esters by distillation (rectification), it may also be expedient to carry out the novel process in such a way that at least one inhibitor component to be fed in is added not continuously but merely from time to time, i.e. at recurrent intervals (e.g. at the top of the column, at the bottom and/or in the feed).

Everything stated about stabilization during the isolation of (meth)acrylic esters from acid-catalyzed esterification mixtures by distillation (rectification) also applies in the same way to isolation of (meth)acrylic acid or (meth) acrolein from mixtures containing them by distillation (rectification).

(Meth)acrylic acid is obtainable, inter alia, by catalytic gas-phase oxidation of alkanes, alkanols, alkenes or alkenals which contain 3 or 4 carbon atoms. (Meth)acrylic acid is particularly advantageously obtainable, for example, by catalytic gas-phase oxidation of propane, propene, tert-butanol, isobutene, isobutane, isobutyraldehyde or methacrolein. However, other possible starting compounds are those from which the actual $C_3$-/$C_4$-starting compound is first formed as an intermediate during the gas-phase oxidation. An example is the methyl ester of tert-butanol.

These starting gases, as a rule diluted with inert gases such as nitrogen, CO, $CO_2$, saturated hydrocarbons and/or steam, are mixed with oxygen and then passed at elevated temperatures (usually from 200 to 400° C.) and, if required, superatmospheric pressure over transition metal (e.g. Mo-, V-, W- and/or Fe-containing) mixed oxide catalysts and converted by oxidation into (meth)acrylic acid.

Owing to the numerous simultaneous and subsequent reactions taking place in the course of the catalytic gas-phase oxidation and because of the inert dilution phase to be used concomitantly, however, the catalytic gas-phase oxidation gives not pure (meth)acrylic acid but a reaction mixture which essentially contains (meth)acrylic acid, the inert diluent gases and byproducts and from which the (meth)acrylic acid has to be isolated. In addition to byproducts, such as acetic acid, which are comparatively simple to remove from (meth)acrylic acid and are less troublesome in subsequent uses of the (meth)acrylic acid, the reaction mixture also frequently contains lower aldehydes, such as formaldehyde, acetaldehyde, acrolein, methacrolein, propionaldehyde, n-butyraldehyde, benzaldehyde, furfural and crotonaldehyde, which are closely related to (meth)acrylic acid and are therefore difficult to separate from (meth)acrylic acid, and may additionally contain maleic anhydride (the total amount of these byproducts, which are frequently very troublesome in subsequent uses, is as a rule≦2% by weight and in general≧0.05% by weight, based on the amount of (meth) acrylic acid contained in the reaction mixture).

It is also feasible to isolate acrylic acid from the reaction mixture of the catalytic gas-phase oxidation of propylene and/or acrolein by countercurrent adsorption using a high-boiling inert hydrophobic organic liquid. The inhibitor composition can be injected directly into the gas stream or into the apparatus for the countercurrent adsorption. Suitable organic liquids for the countercurrent adsorption include higher alcohols or esters thereof (in particular those with (meth)acrylic acid). The process is essentially carried out in such a way that the reaction mixture is fed countercurrently to the descending adsorption liquid in a conventional adsorption column, the readily volatile byproducts which can be easily separated off are then substantially removed from the liquid discharge of the adsorption column, essentially composed of acrylic acid, the adsorbent and byproducts, by stripping with inert gas in a desorption column, and thereafter the liquid discharge of the desorption column, containing the (meth)acrylic acid and the adsorbent as main components, is treated by rectification to isolate crude acrylic acid.

The problem of isolation of (meth)acrylic acid by rectification also arises when the (meth)acrylic acid is first taken up in water from the reaction gases of the catalytic gas-phase oxidation and the water is then separated off by rectification from the aqueous (meth)acrylic acid-containing mixtures with addition of an organic azeotropic entraining agent.

However, the problem also exists in the preparation of pure acrylic acid (purity>99.7% by weight) from crude acrylic acid (purity>99% by weight) by rectification.

The novel inhibitor composition can be used in the case of all of the abovementioned rectification problems. Of course, the novel inhibitor composition can also be used in the extraction of the (meth)acrylic acid from the reaction mixture of the gas-phase oxidation. The inhibitor composition can be injected directly into the gas stream. Stabilization is also recommended with the separation of mixtures containing (meth)acrylic acid or its esters by crystallization.

(Meth)acrolein is obtainable in a manner corresponding to (meth)acrylic acid, for example by catalytic gas-phase oxidation. However, the oxidation is not continued after the first oxidation stage. Rather, the (meth)acrolein contained in the reaction gas mixture is as a rule first isolated from the reaction gas mixture by extraction with water and then obtained from the aqueous solution by distillation (rectification). For all process steps mentioned, the novel inhibitor composition is suitable for stabilization.

The synergistic activity of the novel inhibitor composition is applicable essentially independently of the pH and both to low temperatures (e.g. room temperature) and to elevated temperatures, as are usual, for example, in thermal physical separation processes as well as for chemical reactions taking place at elevated temperatures.

In particular, the abovementioned applies to the stabilization of (meth)acrylic acid and/or its esters, whose ethylenically unsaturated double bond is particularly active with respect to free radical polymerization.

As a rule, the inhibitor composition is chosen so that the components contained in said composition are completely soluble in the substance to be stabilized, in the amount thereof which is used. Frequently, they are added not as pure substance but as a suspension, emulsion or solution. Particularly suitable solvents and/or dispersing media are those substances which are part of the system to be stabilized, i.e., for example in chemical reactions, such as esterifications, all starting materials and products.

The Example which follows illustrates the invention.

EXAMPLE

Various stabilizers were added in different amounts in each case to 1 ml of acrylic acid and the mixture was enclosed gastight, under air, in glass ampoules (1.9 ml internal volume). The ampoules were completely immersed in an oil bath at 120° C. and stored in the absence of light.

The time until the acrylic acid had completely polymerized was then determined. The time when the solidification of the polymerization mixture was detectable was determined visually. The Table below shows the added amounts of the components of the inhibitor and, correspondingly, the time taken for the corresponding polymerization mixture to become solid.

| Experiment No. | HO-TEMPO (ppm) | $H_3PO_3$ (ppm) | MEHQ (ppm) | Time (min) |
|---|---|---|---|---|
| 1 | 10 | | | 77 |
| 2 | | 25 | | 16.5 |
| 3 | | | 50 | 55 |
| 4 | | 25 | 50 | 71.5 |
| 5 | 10 | 25 | | 110 |
| 6 | 10 | | 50 | 214 |
| 7 | 10 | 25 | 50 | 319 |

Data in each case in ppm by weight, based on the acrylic acid added

HO-TEMPO: 4-Hydroxy-1-oxyl-2,2,6,6-tetramethylpiperidine

MEHQ: Hydroquinone monomethyl ether

The experimental results show that, when all three inhibitor types are used—i.e. compounds which have a phosphorus atom in the oxidation state +3, nitroxyl radical (derivatives) and phenol (derivatives)—the time taken for the corresponding sample to become solid is found to be particularly long. This shows that the synergistic activity (the mutual enhancement of the inhibiting effect of the individual components) of this three-component composition is particularly pronounced.

We claim:

1. A mixture containing at least one compound which has at least one vinylically unsaturated group and an inhibitor composition comprising as components, a) a compound having at least one nitroxyl radical, b) at least one phenol derivative and c) at least one further chemical compound which contains at least one phosphorus atom which has the oxidation state +3.

2. The mixture according to claim 1, wherein the nitroxyl radical used is 4-hydroxyl-1-oxyl-2,2,6,6-tetramethylpiperidine.

3. The mixture according to claim 1, wherein the compound which contains at least one phosphorus atom is orthophosphorous acid or an ester of orthophosphorous acid.

4. The mixture according to claim 1, wherein the phenol derivative is selected from the group consisting of a phenol or cresol in which one or more hydrogen atoms have been, substituted by tert-butyl groups and a hydroquinone.

5. The mixture according to claim 1, wherein the chemical compound which contains at least one phorphorus atom has a concentration of from 1 to 5000 ppm, the natroxyl radical has a total concentration of from 1 to 3000 ppm, and one or more phenol dedvatives having a total concentration of from 1 to 3000 ppm.

6. The mixture according to claim 5, wherein the chemical compound which contains at least one phosphorus atom has a total concentration of from 5 to 1000 ppm, the nitroxyl radical has a total concentration of from 5 to 300 ppm, and the one or more phenol derivatives have a total concentration of from 5 to 1500 ppm.

* * * * *